United States Patent [19]

Mecca

[11] 3,970,748
[45] July 20, 1976

[54] ALUMINUM CHLORHYDROXY GLYCINATE COMPLEXES
[75] Inventor: Sebastian B. Mecca, Abington, Pa.
[73] Assignee: Schuylkill Chemical Company, Philadelphia, Pa.
[22] Filed: Feb. 24, 1975
[21] Appl. No.: 552,316

[52] U.S. Cl. .............................. 424/68; 260/448 R
[51] Int. Cl.² ............................................. A61K 7/38
[58] Field of Search ................... 260/448 R; 424/68

[56] References Cited
UNITED STATES PATENTS

| | | |
|---|---|---|
| 2,480,743 | 8/1949 | Krantz et al. ................... 260/448 R |
| 2,508,787 | 5/1950 | Grote et al. ...................... 260/448 R |
| 2,910,493 | 10/1959 | Rinse et al. ..................... 260/448 R |
| 3,359,169 | 12/1967 | Slater et al. ................... 260/448 AD |
| 3,632,596 | 1/1972 | Mecca ............................. 424/68 X |
| 3,792,068 | 2/1974 | Luedders et al. ............... 260/448 R |

Primary Examiner—Helen M. S. Sneed
Attorney, Agent, or Firm—Howson and Howson

[57] ABSTRACT

An aluminum chlorhydroxy glycinate complex is disclosed as is an aluminum chlorhydroxy propylene glycol glycinate complex. Medicinal and cosmetic compositions containing these complexes are also disclosed.

4 Claims, No Drawings

ALUMINUM CHLORHYDROXY GLYCINATE COMPLEXES

BACKGROUND OF THE INVENTION

Aluminum compounds, particularly those formed through the reaction of aluminum chlorhydroxides and hydroxylic compounds such as a polyhydroxy alkyl compound, e.g. propylene glycol, are known to be useful in antiperspirant compositions. U.S. Pat. No. 3,359,169 describe such compounds. An alcohol soluble aluminum allantoin propylene glycol complex, likewise useful in antiperspirant compositions, is described in U.S. Pat. No. 3,632,596.

Gylcine (aminoacetic acid) is an amino acid which may be formed by ammonolysis of chloroacetic acid (see Kirk-Othmer, Encyclopedia of Chemical Technology, 2nd Edition, Vol. 2, p. 350, Interscience, 1963). Glycine is a simple amino acid and has found use, for example, when reacted with an aluminum derivative of isopropyl alcohol as a gastric antacid (Kirk-Othmer, Encyclopedia of Chemical Technologoy, 2nd Edition, Vol. 2, p. 430, Interscience, 1963).

It is an object of this invention to provide novel complexes containing aluminum chlorhydroxide or aluminum chlorhydroxy propylene glycol and glycine which are stable, both in dry form and in solutions and are not sensitive to heat and which may be utilized in a variety of cosmetic formulations for their beneficial effects.

DETAILED DESCRIPTION OF THE INVENTION

The present invention relates to novel complexes of aluminum chlorhydroxide or aluminum chlorhydroxide propylene glycol and glycine and, more particularly, to an aluminum chlorhydroxy glycinate complex and an aluminum chlorhydroxy propylene glycol glycinate complex.

The novel complexes of this invention may be depicted as having the formulas:

$[Al_2(OH)_4Cl]_x \cdot [H_2NCH_2COOH]_y$ (aluminum chlorhydroxy glycinate) and $[[Al_2(OH)_4Cl][C_3H_8O_2]]_x \cdot [H_2NCH_2COOH]_y$ (aluminum chlorhydroxy propylene glycol glycinate) wherein $x$ and $y$ are each about 1 and refer to the number of mols of each component. In the foregoing formulas, $Al_2(OH)_4Cl$ represents aluminum chlorhydroxide, $H_2NCH_2COOH$ represents glycine and $C_3H_8O_2$ represents propylene glycol.

It is not necessary to utilize special reaction conditions to form the desired complexes. The complexes may be formed by a procedure in which the aluminum chlorhydroxide or aluminum chlorhydroxy propylene glycol are combined with glycine and formed into a uniformly mixed damp mass with the addition of small quantities of water. The dmp mass is then dried at 160° to 180°F. until the product is dry and has a relatively constant weight. In another procedure, boiling water is added to a mixture of aluminum chlorhydroxide or aluminum chlorhydroxy propylene glycol and glycine. The amount of water used in the reaction is not critical so long as an amount is utilized sufficient to wet the intimate mixture of reactants and form a slurry or solution of the reactants. After the reaction is complete, water is preferably removed from the product to a level below about 1%, by weight, based on the weight of the complex. This may be accomplished by heating the complex to a temperature of from about 150°F. to about 160°F. until the product is dry and has a relatively constant weight. Any drying means, including spray drying, may be employed, and vacuum may be employed to assist drying.

It has also been found that the desired complexes may be prepared in a solid state reaction in which aluminum chlorhydroxide or aluminum chlorhydroxy propylene glycol are combined with glycine and thoroughly blended to form a uniform mixture. The mixture is then passed through a micronizer where the material is pulverized to an extremely fine size (generally less than 10 microns) and intimately admixed with the formation of the desired complex occurring in a solid state reaction.

The relative proportions of aluminum chlorhydroxide or aluminum chlorhydroxy propylene glycol and glycine utilized in forming the desired complexes may vary somewhat. Regardless of the proportions, however, the products are complex chemical compounds in which the components are chemically bound.

In the complexes of this invention, the aluminum chlorhydroxide or aluminum chlorhydroxy propylene glycol are preferably combined with glycine in a mol ratio of about 1 to 1. Therefore, in the preferred embodiments of this invention aluminum chlorhydroxide and glycine are combined in a mol ratio of about 1 to 1 to form the aluminum chlorhydroxy glycinate complex. Likewise, aluminum chlorhydroxy propylene glycol and glycine are combined in a mol ratio of about 1 to 1 to form the aluminum chlorhydroxy propylene glycol glycinate complex.

It has been found that the complexes produced as the result of the present invention are remarkably stable whether in solution (aqueous or alcohol) or heated. The complexes have the combined attributes of the aluminum containing compound and glycine, e.g. the astringent, bacteriostatic properties of the aluminum chlorhydroxide component and the buffering, moisturizing and conditioning properties of glycine. The complexes are thus useful in a myriad of topical preparations such as deodorants, antiperspirants and the like.

The complexes have been found to be especially useful in antiperspirant-deodorant products especially antiperspirant-deodorant products formulated with aluminum salts such as aluminum sulfate, aluminum chloride and aluminum chlorhydroxide. Such products cause staining, destruction or charring of wearing apparel which becomes impregnated with the aluminum salts through contact with those areas of the body where the antiperspirant-deodorant products have been applied. High temperatures encountered in laundering, ironing or pressing the apparel causes the impregnated aluminum salts to decompose forming their corresponding aluminum acids which cause the undesired staining and possible charring and destruction of the clothing.

Surprisingly, it has been found that formulating antiperspirant-deodorant products with the complexes of this invention eliminates the undesired staining and destruction of clothing. It is thought that the heat encountered in laundering causes ammonia to be released from the glycine component of the complex. The ammonia neutralizes the acid produced through decomposition of the aluminum salt portion of the complex, thereby eliminating the destructive effects of the acid.

It has further been found that the glycine phase of the complex acts as a buffer for any free acid liberated through body heat or perspiration. The complex thus contributes "built-in" anti-staining and buffering action to antiperspirant-deodorant products. The built-in buffering action imparts anti-irritant and hypoallergenic properties to antiperspirant-deodorant products, especially those products containing the aluminum chlorhydroxy glycine complex, thereby increasing the spectrum of persons who can utilize such products without adverse effects.

The following examples illustrate the preparation of typical complexes and the properties and suggested uses for the complexes. The examples are illustrative only and not intended to limit the scope of the invention.

EXAMPLE 1

190 g. of aluminum chlorhydroxide are thoroughly mixed with 75 g. of glycine. 10 cc. of distilled water is then added and the mixture is triturated until a uniformed mixed damp mass is formed. The resulting mass is then dried for ½ to 1 hour at 160° to 180°F. to a dry-granular powder. The product is an aluminum chlorhydroxy glycinate complex having the formula:

$$[Al_2(OH)_4Cl]_x \cdot [H_2NCH_2COOH]_y$$

where $x$ and $y$ are each about 1 based on glycine and $Al_2O_3$ content. A 20% aqueous solution of the complex has a pH of about 4.5 to about 6. The complex is soluble to the extent of 40 to 50% in water at 25°C. and 75% in boiling water. The complex may be formulated in pharmaceutically acceptable carriers at levels of from about 10 to about 25%, by weight, based on the weight of the product to form an antiperspirant composition. A like complex is formed by suspending 190 g. of aluminum chlorhydroxide and 75 g. of glycine in 200 cc. of boiling, distilled water, followed by evaporating the reaction mixture to dryness under reduced pressure at 150° to 160°F. Similarly, a like complex is formed by thoroughly blending 190 g. of aluminum chlorhydroxide with 75 g. of glycine and micronizing the mixture to a particle size less than 10 microns. An aerosol antiperspirant-deodorant of the following formulation may be prepared with the aluminum chlorhydroxy glycinate complex:

| | % W.W. |
|---|---|
| Aluminum Chlorhydroxy Glycinate Complex | 9 |
| Noval | 3 |
| Crodafos N-10 acid | 0.5 |
| Crodafos N-10 neutral | 0.5 |
| Alcohol | 41.75 |
| Perfume | 0.25 |
| Propellant | 45 |

Dissolve the aluminum chlorhydroxy glycinate complex in a portion of the alcohol with vigorous agitation and heat to 50°C. Combine the additional ingredients with stirring and filter producing a concentrate which may be filled in corrosion resistant cans with the propellant in manners known in the art.

EXAMPLE 2

230 g. of aluminum chlorhydroxy propylene glycol are thoroughly mixed with 75 g. of glycine, 10 cc. of distilled water is then added and the mixture is triturated until a uniformly mixed damp mass is formed. The resulting mass is then dried for ½ to 1 hour at 160°F. to 180°F. to a granular powder. The product is an aluminum chlorhydroxy propylene glycol glycinate complex having the formula:

$$[[Al_2(OH)_4Cl][C_3H_8O_2]]_x \cdot [H_2NCH_2COOH]_y$$

where $x$ and $y$ are each about 1 based on glycine and $Al_2O_3$ content. A 20% solution of the complex has a pH of about 4.5 to about 6.5. The complex is soluble in alcohol and water. The complex may be formulated in pharmaceutically acceptable carriers at levels of from about 10 to about 25%, by weight, based on the weight of the product to form an antiperspirant composition. A like complex is formed by suspending 230 g. of aluminum chlorhydroxy propylene glycol and 75 g. of glycine in 200 cc. of boiling, distilled water, followed by evaporating the reaction mixture to dryness under reduced pressure at 150°to 160°F. Similarly, a like complex is formed by thoroughly blending 230 g. of aluminum chlorhydroxy propylene glycol and 75 g. of glycine and micronizing the mixture to a particle size less than 10 microns.

Having thus described the invention, what is claimed is:

1. An aluminum chlorhydroxy glycinate complex of the formula $[Al_2(OH)_4Cl]_x \cdot [H_2NCH_2COOH]_y$ wherein $x$ and $y$ are each about 1.

2. An aluminum chlorhydroxy propylene glycol glycinate complex of the formula $$[[Al_2(OH)_4Cl][C_3H_8O_2]]_x \cdot [H_2NCH_2COOH]_y$$

wherein $x$ and $y$ are each about 1.

3. Antiperspirant-deodorant compositions comprising from about 10 to about 25%, by weight, based on the weight of the composition, of the aluminum chlorhydroxy glycinate complex of claim 1 and a pharmaceutically acceptable carrier.

4. Antiperspirant-deodorant compositions comprising from about 10 to about 25%, by weight, based on the weight of the composition, of the aluminum chlorhydroxy propylene glycol glycinate complex of claim 2 and a pharmaceutically acceptable carrier.

* * * * *